(12) United States Patent
Knispel

(10) Patent No.: US 7,926,359 B2
(45) Date of Patent: Apr. 19, 2011

(54) EQUIPMENT AND METHOD TO DETECT FLEXIBLE DEVICES

(75) Inventor: Peter Knispel, Constance (DE)

(73) Assignee: Siemens Aktiengesellschaft, Munich (DE)

( * ) Notice: Subject to any disclaimer, the term of this patent is extended or adjusted under 35 U.S.C. 154(b) by 302 days.

(21) Appl. No.: 12/176,662

(22) Filed: Jul. 21, 2008

(65) Prior Publication Data

US 2009/0019942 A1    Jan. 22, 2009

(30) Foreign Application Priority Data

Jul. 20, 2007   (DE) .......................... 10 2007 034 070

(51) Int. Cl.
  *G01N 3/20*   (2006.01)
(52) U.S. Cl. ....................................................... 73/852
(58) Field of Classification Search ................... 73/852, 73/849, 159, 78
  See application file for complete search history.

(56) References Cited

U.S. PATENT DOCUMENTS

| | | | |
|---|---|---|---|
| 3,158,021 A | | 11/1964 | Walters et al. |
| 4,991,432 A | * | 2/1991 | Houghton et al. ............... 73/159 |
| 5,171,403 A | * | 12/1992 | Chase et al. ................... 162/197 |
| 5,373,933 A | * | 12/1994 | Planke et al. ............... 198/689.1 |
| 6,032,517 A | * | 3/2000 | Reisig et al. ....................... 73/78 |
| 7,096,743 B2 | * | 8/2006 | Vogel et al. ...................... 73/849 |
| 7,186,317 B2 | * | 3/2007 | Beuther et al. ................ 162/109 |
| 7,194,916 B2 | * | 3/2007 | Ouellet et al. ................... 73/852 |
| 7,669,470 B2 | * | 3/2010 | Sanford .......................... 73/159 |

FOREIGN PATENT DOCUMENTS

| | | |
|---|---|---|
| DE | 1648751 | 4/1971 |
| DE | 1574164 | 11/1971 |
| DE | 1574165 | 11/1971 |
| DE | 69000164 T2 | 10/1990 |
| WO | 2004030835 A1 | 4/2004 |

* cited by examiner

*Primary Examiner* — Lisa M Caputo
*Assistant Examiner* — Octavia Davis

(57) ABSTRACT

A device and a method are provided for checking whether when an object has a sufficiently. The object to be examined extends in an object plane. A force exertion device exerts a force on the held object such that the force includes a force component at right angles to the object plane. A fan generates a flow of a fluid which hits a movement area of the object. A holding device holds the object so that the object is held flat in a holding subsurface of the object plane and is movable in a movement area located outside the holding subsurface at right angles to the object plane. A measuring device tests whether the force produced by the force exertion device causes the movement area of the object to be deflected by a distance at right angles to the object plane which is greater than a predetermined limit.

8 Claims, No Drawings

EQUIPMENT AND METHOD TO DETECT FLEXIBLE DEVICES

CROSS REFERENCE TO RELATED APPLICATIONS

This application claims priority of German application No. 10 2007 034 070.4 DE filed Jul. 20, 2007, which is incorporated by reference herein in its entirety.

FIELD OF INVENTION

The invention relates to a device and a method for checking whether a flat subject has a sufficiently great stiffness or not.

SUMMARY OF INVENTION

A device and a method with the features of the preamble of the independent claims are known from U.S. Pat. No. 3,158,021. The object to be examined in this patent is a lumber product which extends in one object plane. This object is clamped between a number of conveyor belts such that at its two ends it cannot be deflected at right angles to the object plane, but is fixed. Between these two clamping areas an arrangement with two rollers exerts a predefined force at right angles to the object plane. This force causes a deflection of the lumber product, with the size of said deflection depending on the stiffness of the lumber product. If the deflection reaches or exceeds a predetermined limit the deflected lumber product closes a contact which triggers the generation of a signal.

The flat object is for example a flat mail item, e.g. a letter. The object is to be processed automatically by a system, e.g. a sorting system. In such cases it must be ensured that the object has a sufficiently great stiffness. If it does not, the object cannot be processed automatically because it could be damaged and it must be removed from the system.

The task of examining the stiffness of a mail item is presented for example in DE 69000164 T2. A sorting system can only process the mail item if it has a sufficient stiffness. In DE 69000164 T2 the mail item is fed through between three parallel rods which are arranged in one plane and two opposing pressure rods. A weight is connected to the two opposing pressure rods. This weight causes a deflection of the mail item which is measured and is a measure of the stiffness.

WO 2004/030835 A1 describes how the stiffness of a mail item is able to be measured during transport in a sorting system. The mail item, e.g. a flat letter, is clamped into a clamping area between two conveyor belts in each case. Very short mail items are clamped in only one clamping area. A guide surface or guide roller exerts a defined force at right angles to the object surface of the letter. Once again the deflection is measured. In one embodiment a laser distance sensor measures the distance by which a delimiting surface of the mail item is deflected. Additionally the thickness of the mail item is measured and account is taken of the deflection during the calculation.

Similar facilities for measuring the stiffness of mail items are also described in 1574165 A, DE 1574164 A and DE 1648751 A. These facilities also effect a deflection of a mail item by means of guide rollers or guide surfaces.

The object of the invention is to provide a facility and a method with the features of the preamble of the independent claims which manage with a more simple mechanical design than existing facilities and methods.

The object is achieved by a device and a method with the features of the independent claims. Advantageous embodiments are specified in dependent claims.

The facility is embodied to test whether a flat object possesses sufficiently great stiffness or not. The flat object to be examined extends in one object plane.

The test facility includes a holder device, a drive, a force exertion device and a measuring device.

The holder device is embodied to hold the object so that the object is held flat in a holding subsurface of the object plane. It might further hold the object so that the object is movable in a movement area outside the holding subsurface, and yet is still movable in at least one direction at right angles to the object plane.

The drive is equipped to move the object held by the holder device relative to the force exertion device. It is possible for the drive to move the holder device along with the held object. It is also possible for the drive to move the force exertion device and to move it past the object for example. It is also possible for the drive to move the holder device with the object and also the force exertion device, and in doing so to initiate the relative movement.

The force exertion device is embodied to apply a force to the held object such that the force includes a force component at right angles to the object plane. The force component acts on the object in the movement area.

The measuring device is embodied to test whether the force produced by the force exertion device causes the movement area of the object to be deflected by a distance at right angles to the object plane which is greater than a predetermined limit.

A force is exerted on the flat object on a trial basis. The measuring device measures whether this force causes a deflection of the object at right angles to the object plane which is greater than a predetermined limit. If so, it is decided that the stiffness of the object is not great enough.

According to the solution the force exertion device includes a fan. This fan creates a flow of a fluid which hits the movement area of the object. This flow exerts the force which causes the trial deflection of the object.

The device and the method can be used during system operation. It is not necessary to remove the object to be examined from ongoing processing. The invention obviates the need to measure the thickness or the weight of the object.

The device according to the invention does not require the object to be clamped in a number of clamping areas.

The deflection can be effected in a non-contact manner. This reduces the danger of the object being damaged by the testing. This danger arises for example when the object is a freshly printed mail item and the print ink is not yet dry.

Preferably the object is moved past a force exertion device embodied as a fixed device. This embodiment makes it especially simple to incorporate the device into a processing system, e.g. a sorting system for mail items, in which the object is being transported in any event.

BRIEF DESCRIPTION OF THE DRAWINGS

The invention is described below with reference to an exemplary embodiment. The sole FIGURE shows an overhead view of the test device.

DETAILED DESCRIPTION OF INVENTION

In the exemplary embodiment the object of which the stiffness is to be automatically determined is a flat mail item, e.g. a large letter. A sequence of flat mail items arrives in a sorting center. These mail items are to be processed by a sorting system. This sorting system automatically reads the delivery address of each mail item and extracts the mail item depending on the recognized delivery address into one of many output compartments. In such cases each mail item is transported through the sorting system. When this is done the direction of transport is changed more frequently.

Each flat mail item extends in an object plane. It is possible that a mail item is not stiff enough and that only a too low force is required in order to deflect the mail item at right angles to the object plane. If such a mail item (also referred to as a "flimsy mail item") were to be processed together with the other mail items by the sorting system, there is the danger of the mail item that is not stiff enough being damaged or even destroyed on its journey through the sorting system. In addition the transport of this mail item can cause a blockage, especially before an output compartment, because the mail item becomes creased for example.

It would not be sufficient to merely measure the thickness of each mail item. Mail items of equal thickness can have significantly different degrees of stiffness for example, since their respective content differs in its stiffness. It is thus necessary, for each mail item of the sequence, to test whether the mail item possesses a stiffness sufficient for automatic processing or not.

A mail item that does not possess sufficient stiffness is extracted by the shortest paths into a special output compartment and preferably manually processed.

The FIGURE shows a schematic overhead view of the test device. Two mail items are shown in this example: One mail item B1 and a subsequent mail item B2. Mail items B1, B2 are transported in a direction of transport T. In the exemplary embodiment the direction of transport T lies in the object plane. The object plane lies at right angles to the plane of the drawing of the FIGURE.

In the exemplary embodiment the test device includes the following components:
- a force exertion device 1 in the form of a fan with a power supply 2,
- a light barrier with a light source 3 and a receiver 4,
- a guide plate 5 for stabilizing the mail items,
- a further guide plate 6 for aligning the mail items,
- a contact sensor in the guide plate 5,
- a first endless conveyor belt EF1 which is routed around one driven pulley 8 and two non-driven pulleys 9, 10, and
- a second endless conveyor belt EF2, which is routed around one driven pulley 1 and two non-driven pulleys 12, 13.

The mail item B1 is held and transported by this holder device. The mail item B2 currently being examined is held by two endless conveyor belts that are the same as the two endless conveyor belts EF1, EF2. These have been excluded from the FIGURE for reasons of clarity. The two endless conveyor belts not shown that move a mail item past fan 1 and in the situation of the FIGURE are currently holding the mail item B2, function together as a holder device as defined in the claims.

The endless conveyor belts EF1, EF2 hold a mail item flat in a strip that extends in the direction of transport T over the length of the mail item. The area of the mail item lying above this strip is movable at right angles to the object plane and thus also at right angles to the direction of transport T and functions as a movement area of the flat object.

The fan 1 exerts a force F on the held object. In the embodiment shown in the FIGURE the force F acts at right angles on the object plane and thus also at right angles to the direction of transport T. In the situation shown in the FIGURE it acts on object B2. In another embodiment the force F acts at an angle to the object plane. In both embodiments the force F exerted has a force component at right angles to the object plane.

Preferably the fan 1 blows air from the environment against the mail item B2 to be examined. In dusty or fire-hazard environments it is however typically advantageous for the fan to instead pump out a fluid (gas or liquid) from a storage container and blow it against the mail item B2 to be examined.

The effect of the force F produced by the fan is to deflect the movement area of the object by a distance at right angles to the object plane. In the exemplary embodiment the force causes a deflection at right angles to the direction of transport T, i.e. in the FIGURE a deflection to the right. The FIGURE shows that—viewed in the direction of transport T—the rear upper corner of mail item B2 is strongly bent.

In the exemplary embodiment the mail item B1 has already passed the test device. It has been established that the mail item B1 has a sufficiently great stiffness. The fan 1 has only been able to deflect the mail item B1 by a slight distance (much less than dist). The light barrier has not registered a deflection greater than dist.

The test device is now examining mail item B2. The fan 1—viewed in the direction of transport T—causes the rear upper corner of mail item B2 to be bent over and thereby deflected.

The transmitter 3 of the light barrier emits a light beam LS or even an infrared beam, and does this in parallel to the object plane and in the exemplary embodiment thus in the direction of transport T. The receiver 4 measures whether the light beam LS from the transmitter 3 arrives at full strength or whether the deflected mail item B2 interrupts or at least weakens the light beam. So that the deflected mail item B2 interrupts the light beam LS, the deflection must be the same or greater than a predetermined limit dist. This distance dist is simultaneously the distance between the object plane of the object, while the latter is being moved past the force application device 1, and the light beam LS.

If a deflected mail item interrupts the light beam LS, the deflection is the same or greater than dist. In this case a decision is automatically taken that the stiffness of the mail item is not large enough. In the example shown in the FIGURE mail item B1 has a sufficiently great stiffness whereas mail item B2 is not stiff enough since the deflected mail item B2 interrupts the light beam LS.

In the exemplary embodiment the deflection of mail item is at its greatest at the topmost edge. Preferably the light barrier 3, 4 is designed so that the light beam LS has a sufficiently large coverage in the vertical direction to detect mail items of different height.

Preferably a suitable value for dist is determined empirically. To this end mail items which have a sufficient stiffness and also mail items which are not stiff enough are transported for trial purposes by the device of the FIGURE and in this case are routed past the fan 1. The fan 1 creates the same force each time, which acts on the mail item. The size of the deflection is measured for sufficiently stiff and for insufficiently stiff mail items. The value dist is set so that the light beam LS will only be interrupted by insufficiently stiff mail items. If the available space is not sufficient to achieve a distance dist between light beam LS and object plane, the force F that the fan 1 exerts on the mail item will preferably be reduced. Conversely it is possible to increase the force if instead a sufficient distinction between stiff and insufficiently stiff mail items is to be achieved.

In the exemplary embodiment the force exertion device 1 is embodied as a stationary device, and an object B1, B2 to be examined is moved past the device 1. An alternate embodiment is however also possible, in which conversely the force exertion device 1 is moved past the object B1, B2 to be examined. For example the fan 1 is mounted on a rail which runs in parallel to the object plane. The fan 1 is guided past the held mail item B1, B2.

In the exemplary embodiment the relative displacement between the object to be examined and the force exertion object 1 occurs in parallel to the object plane. It is also possible for the relative displacement to occur in another direction, for example by the mail item being moved at an angle past the fan 1.

In the exemplary embodiment the device further includes a guide device in the form of a guide plate 5. This guide plate 5 is embodied to limit a deflection of the movement area at right angles to the object plane. A deflection which is too great can actually damage a mail item.

A contact sensor 7 is built into the guide plate 5 in the exemplary embodiment. This contact sensor 7 measures whether a mail item touches the guide plate 5 or not. If a mail item touches the guide plate 5 the fan 1 has produced a deflection which is much greater than dist. In this case the stiffness of the mail item is particularly small. The mail item B2 in the example of the FIGURE will touch the contact sensor 7. From this it is detected that it has an especially low stiffness.

A further guide plate 6 realigns a mail item which has got into a angled position because of the air from the fan 1. The mail items must be in an almost perpendicular position to enable them to be further processed or extracted without being damaged.

A mail item with a stiffness that is too low and which is thus deflected by a distance of dist or more has too low a stiffness. It will be automatically diverted into a special output compartment. In the example shown in the FIGURE mail item B2 is removed into this special output compartment. It is not processed further by the sorting system but is processed manually.

LIST OF REFERENCE SYMBOLS

| Reference symbol | Meaning |
|---|---|
| 1 | Force exertion device in the form of a fan |
| 2 | Power supply of the fan 1 |
| 3 | Light source of the light barrier |
| 4 | Receiver of the light barrier |
| 5 | Guide plate for stabilizing the mail items |
| 6 | Guide plate for aligning the mail items |
| 7 | Contact sensor in the guide plate 5 |
| 8 | Driven pulleys of the endless conveyor belt EF1 |
| 9, 10 | Non-driven pulleys of the endless conveyor belt EF1 |
| 11 | Driven pulleys of the endless conveyor belt EF2 |
| 12, 13 | Non-driven pulleys of the endless conveyor belt EF2 |
| B1 | First letter; has sufficient stiffness |
| B2 | Second letter; does not have sufficient stiffness |
| dist | Predetermined limit: if the deflection is greater than dist, the stiffness of the mail item is too small |
| EF1 | First endless conveyor belt |
| EF2 | Second endless conveyor belt |
| F | Force exerted by fan 1 |
| LS | Light beam emitted by transmitter 3 |
| T | Direction of transport |

The invention claimed is:

1. A test device for testing an object for sufficient stiffness, comprising:
   a holder device holds an object extending in an object plane, the holder device holds the object so that the object is held flat in a holding subsurface of the object plane and is movable at right angles to the object plane in a movement area outside the holding subsurface,
   a force exertion device exerts a force on the held object such that the exerted force includes a force component at right angles to the object plane, the force exertion device includes a fan to exert the force by generating a flow of a fluid hitting the movement area;
   a drive moves the object held by the holder device relative to the force exertion direction; and
   a measuring device tests when the force produced by the force exertion device causes the movement area of the object to be deflected by a distance at right angles to the object plane that is greater than a predetermined limit,
   wherein when the deflection is greater than the predetermined limit the object does not possess a sufficient stiffness;
   wherein the measuring device includes a light barrier arranged so that the movement area of the object interrupts a light beam of the light barrier when the movement area is deflected by a distance at right angles to the object plane which is greater than the predetermined limit,
   wherein the holder device transports the object in a direction of transport that lies in the object plane, and
   wherein the distance between the object plane and the light beam emitted by the light barrier is equal to the predetermined limit.

2. The test device as claimed in claim 1, wherein the force exertion device is a stationary device.

3. The test device as claimed in claim 1, wherein the holder device includes an endless conveyor belt and an opposing conveyer element in order to hold the object in the holding part surface so that the object is clamped and transported, and the drive transports the held object by turning the endless conveyor belt.

4. The test device as claimed in claim 1, further comprises a guide device to limit a deflection of the movement area at right angles to the object plane.

5. The test device as claimed in claim 4, wherein the force exertion device and the guide device are stationary devices and the exerted force deflects the object onto the guide device.

6. The test device as claimed in claim 1, wherein the measuring device includes a contact sensor arranged so that the sensor is activated when the movement area of the object is deflected by a distance at right angles to the object plane that is greater than the predetermined limit.

7. The test device as claimed in claim 6,
   wherein the contact sensor is built into a guide device, the guide device limits a deflection of the movement area at right angles to the object plane, and
   wherein the contact sensor measures the deflected object touching the guide device.

8. A method for testing that an object possesses a sufficient stiffness, comprising:
   holding the object in an object plan such that the object is held flat in a holding subsurface of the object plane and is movable in a movement area located outside the holding subsurface at right angles to the object plane;
   moving the held object relative to a force exertion device;
   exerting a force on the held object by the force exertion device, the force includes a force component at right angles to the object plane, the force exertion device includes a fan that exerts the force by generating a flow of a fluid which hits the movement area; and
   checking when the force exerted by the force exertion device causes the movement area of the object to be deflected by a distance at right angles to the object plane that is greater than a predetermined limit, wherein when the deflection is greater than the predetermined limit the object does not possess a sufficient stiffness;

wherein said checking includes determining when the deflected object interrupts a light beam of a light barrier, and wherein when the deflected object interrupts the light beam, the deflection is greater than the predetermined limit.

\* \* \* \* \*